United States Patent [19]

Vedros et al.

[11] Patent Number: 4,877,613

[45] Date of Patent: Oct. 31, 1989

[54] PROCESS FOR PREPARING VETERINARY ACELLULAR VACCINES AGAINST GRAM-NEGATIVE NONENTERIC PATHOGENIC BACILLI

[75] Inventors: Neylan A. Vedros, Alameda; Te-ning E. Liu, Martinez, both of

[73] Assignee: Biotech Connections, Inc., San Leandro, Calif.

[21] Appl. No.: 81,942

[22] Filed: Aug. 5, 1987

[51] Int. Cl.[4] .................... A61K 39/02; A07K 3/02; A07K 3/12; A07K 31/24
[52] U.S. Cl. .................................. 424/92; 514/54
[58] Field of Search ......................... 424/92; 514/54

[56] References Cited

U.S. PATENT DOCUMENTS

| | | | |
|---|---|---|---|
| 4,123,520 | 10/1978 | Hagopian | 424/92 |
| 4,220,717 | 9/1980 | Kuo | 435/803 |
| 4,413,057 | 11/1983 | Carlo et al. | 424/92 |
| 4,686,102 | 8/1987 | Ritchey et al. | 424/92 |
| 4,753,796 | 6/1988 | Moreno et al. | 424/92 |
| 4,755,381 | 7/1988 | Cryz | 424/92 |

FOREIGN PATENT DOCUMENTS

| | | | |
|---|---|---|---|
| 709832 | 5/1965 | Canada | 424/92 |
| 594173 | 2/1978 | U.S.S.R. | 424/92 |
| 1084293 | 4/1984 | U.S.S.R. | 424/92 |
| 886597 | 1/1962 | United Kingdom | 424/92 |
| 1426042 | 2/1976 | United Kingdom | 424/92 |

OTHER PUBLICATIONS

Vedros N. A., and Giard, R., Abstract presented at the 13th Annual Conference and Workshop and 7th Eastern Fish Health Workshop, May 1982.
Gotschlich, E. C. (1975) Monogr. Allergy 9: 245–258.
Moreno, C., et al. (1985) Infection and Immunity 47: 527–533.
Moreno, C., Abstract from Medicine Tropicale, 5th International Conference, Mar. 1983.
Lifely, M. R., and Wang, Z. (1988) Infection and Immunity 56: 3221–3227.

*Primary Examiner*—Ronald W. Griffin
*Attorney, Agent, or Firm*—Irell & Manella

[57] ABSTRACT

Surface polysaccharide and somatic polysaccharide are recovered from gram-negative nonenteric pathogenic bacilli in purified forms that are useful as veterinary acellular vaccines either individually or combined. The surface polysaccharide recovery process involves shearing the surface polysaccharide and somatic polysaccharide from the cell membrane, removing the bacteria, isolating the surface polysaccharide by precipitation with Cetavlon, solubilizing the precipitate, and removing nucleic acids by ethanol precipitation. The somatic polysaccharide is recovered from the supernatant remaining after the Cetavlon precipitation by ethanol precipitation.

19 Claims, No Drawings

PROCESS FOR PREPARING VETERINARY ACELLULAR VACCINES AGAINST GRAM-NEGATIVE NONENTERIC PATHOGENIC BACILLI

TECHNICAL FIELD

The present invention is in the fields of veterinary medicine and biochemistry. More specifically it relates to a process for isolating certain biopolymers from gramnegative nonenteric pathogenic bacilli in forms that are useful as veterinary acellular vaccine compositions.

BACKGROUND OF THE INVENTION

Numerous small gram-negative bacilli infect and cause serious disease in animals. Vaccines against these pathogens are normally either killed or attenuated whole cell bacterins. While there are many reports in the literature on studies of the antigenic components of these bacteria, there is little reported respecting commercially viable processes for making acellular (cell-free) or subunit vaccines for these pathogens.

Vedros, N.A., and Giard, R. (Abstract presented at the 13th Annual Conference and Workshop and 7th Eastern Fish Health Workshop, May 1982) disclosed a process for preparing a crude acellular vaccine for *Pasteurella multocida* infections in marine mammals. A culture of the organisms was shaken with glass beads and then centrifuged. The culture supernatant wa treated with ammonium sulfate and the resulting precipitate was alkaline digested and gel filtered to remove low molecular weight materials. The resulting vaccine consisted mainly of surface or capsular polysaccharide with minor amounts of protein and nucleic acids. While the process provided an effective vaccine, it was too complex and costly to provide a commercially viable way to prepare veterinary vaccines on a large scale.

Monogr. Allergy (1975) 9:245–258 describes a process for making a polysaccharide vaccine for preventing meningococcal disease in humans. A culture of *Neisseria meningitidis* was treated with 1% Cetavlon to kill the meningococci and precipitate polysaccharides from solution. The precipitate and bacterial debris were collected by centrifugation and then treated with a calcium chloride solution to dissociate polysaccharide-Cetavlon complexes. Nucleic acids were then precipitated with ethanol and removed. Polysaccharides were precipitated with additional ethanol and washed with ethanol and acetone to remove residual salt and Cetavlon and yield a 50% pure product. Further purification of the polysaccharide was achieved by chloroform-butanol extraction followed by ultracentrifugation or by phenol extraction followed by dialysis and sedimentation. This procedure for making a human vaccine is also too costly and complex to be adapted for producing veterinary vaccines in commercial quantities.

SUMMARY OF THE INVENTION

The invention provides processes for preparing purified forms of surface polysaccharides and purified forms of somatic polysaccharides that are useful individually or combined as veterinary acellular vaccines against gram-negative nonenteric pathogenic bacilli.

The process for preparing the purified surface polysaccharide starts with an aqueous suspension (e.g., culture) of the bacteria and comprises the following steps:

(a) mechanically shearing surface polysaccharide and somatic polysaccharide from the outer membrane of the bacteria without damaging the membrane;

(b) separating the bacteria from the suspension to provide a surface polysaccharide- and somatic polysaccharide-containing supernatant;

(c) adding an organic cationic precipitating agent which does not degrade the surface polysaccharide and somatic polysaccharide to the supernatant to form a precipitate comprising an ionic complex of the agent and the surface polysaccharide;

(d) separating the precipitate of (c) from the supernatant;

(e) solubilizing the separated precipitate of (d) in an aqueous medium under conditions which cause the ionic complex to dissociate;

(f) adding a sufficient amount of lower alkanol to the solution of (e) to cause nucleic acids to precipitate therefrom without substantial coprecipitation of the surface polysaccharide;

(g) separating the precipitate of (f) from the solution;

(h) thereafter increasing the concentration of lower alkanol in the solution to a level which causes the surface polysaccharide to precipitate therefrom; and (i) recovering the surface polysaccharide precipitate of (h).

The process for preparing the purified somatic polysaccharide also starts with an aqueous suspension of the pathogenic bacteria. It involves the following steps:

(a) mechanically shearing surface polysaccharide and somatic polysaccharide from the cell membrane of the bacteria without damaging the cell membrane;

(b) separating the bacteria from the suspension to provide a surface polysaccharide- and somatic polysaccharide-containing supernatant;

(c) adding an organic cationic precipitating agent which does not degrade the surface polysaccharide and somatic polysaccharide to the supernatant to form a precipitate comprising an ionic complex of the agent and the surface polysaccharide;

(d) separating the precipitate of (c) from the supernatant;

(e) thereafter adding a lower alkanol to the supernatant to a concentration which causes the somatic polysaccharide to precipitate therefrom; and (f) recovering the somatic polysaccharide precipitate of (e).

Veterinary subunit vaccines comprising a mixture of the purified forms of surface polysaccharide and somatic polysaccharide described as above in a suitable injectable vehicle are another aspect of the invention.

MODES FOR CARRYING OUT THE INVENTION

The term "surface polysaccharide" intends the acidic extracellular polysaccharide excreted by the bacteria. These polysaccharides are often called "exopolysaccharides". In the case of encapsulated forms of bacteria, the term is synonymous with the term "capsular polysaccharide".

The term "somatic polysaccharide" intends the neutral polysaccharides that are integrally associated with the cell membrane of the bacteria. Somatic polysaccharides are commonly referred to as "lipopolysaccharides" or as "endotoxins".

The process of this invention may be used to make veterinary vaccines against gram-negative nonenteric bacilli which infect animals and whose antigenicity is attributable at least in part to surface (capsular) polysaccharides or somatic (cell membrane) polysaccharides. Examples of such bacteria are Hemophilus bacteria such as *Hemophilus pleuropneumonia* and *Hemophilus somnus*, and Pasteurellae such as *Pasteurella haemolytica* and *Pasteurella multocida*. The vaccines of the invention comprise a purified form of the surface polysaccharide and/or a purified form of the somatic polysaccharide of such bacteria. Preferably, the vaccine contains purified forms of both the surface polysaccharide and somatic polysaccharide.

The bacteria are grown aerobically at physiological temperatures on suitable aqueous growth media. Culture, culture conditions and growth characteristics of gramnegative bacilli are well known in the art. See, for instance, Review of Medical Microbiology (1980) 14th Edition, Lange Medical Publications. The culture may be used directly in the process or the bacteria isolated from the culture and resuspended in an aqueous medium.

The first step in the process is to mechanically shear the acidic surface polysaccharides and neutral somatic polysaccharides from the outer membrane of the bacteria without damaging the outer membrane. This may be accomplished by mildly abrading the membrane with a particulate abrasive means such as glass beads or other like solid particles. The beads will normally be about 5 to 7 mm in diameter and are preferably added to the suspension at 50 to 70 g per liter of suspension. The bead-containing culture is shaken, typically at 100 to 110 rpm for about 48 to 78 hr to achieve the desired shearing of the surface polysaccharides and somatic polysaccharides from the membrane.

The surface polysaccharide- and somatic polysaccharide-containing aqueous phase of the suspension is then separated from the bacteria by centrifugation or other means. The surface polysaccharide is then separated from the aqueous phase by complexing it with an organic cationic precipitating agent that selectively complexes polyanionic polysaccharides without degrading them. Fatty acid quaternary ammonium salts, such as Cetavlon (hexadecyltrimethylammonium bromide), are examples of such agents. The precipitated surface polysaccharide-containing ionic complex is separated from the somatic polysaccharide-containing aqueous phase by centrifugation.

Further purification of the surface polysaccharide is accomplished by dissolving the surface polysaccharide-containing ionic complex in an aqueous medium having a sufficient ionic strength to disassociate the complex, and adding a lower alkanol (i.e., $C_1$ to $C_4$ alkanol, preferably ethanol) to the resulting solution to a concentration that precipitates nucleic acids in the solution without coprecipitating the surface polysaccharide. The concentration of alkanol to accomplish this will normally be in the range of 20% to 25% (v/v). The nucleic acid precipitate may be removed by centrifugation.

The lower alkanol concentration of the resulting surface polysaccharide-containing supernatant is then raised to a level (typically, at least about 80% (v/v)) sufficient to cause the surface polysaccharide to precipitate. The surface polysaccharide precipitate is isolated from the liquid by centrifugation. The precipitate may be dissolved in conventional aqueous parenteral vehicles such as phosphate buffered saline, Ringer's injection, dextrose injection, and the like to form a veterinary acellular vaccine composition. The concentration of surface polysaccharide in the vaccine formulation will usually be in the range of 0.5 to 1 mg/ml (w/v). Alternatively, the surface polysaccharide may be formulated with carriers such as polylactides, polyanhydrides, polyorthoesters and the like to form a sustained release vaccine formulation.

Purification of the somatic polysaccharide from the supernatant remaining after the removal of the surface polysaccharide-containing ionic complex precipitate may be achieved as follows. Optionally, Cetavlon is added to the supernatant to bring down any residual surface polysaccharide. After removal of any precipitate formed, the somatic polysaccharide is precipitated from the supernatant by adding lower alkanol, preferably ethanol, to a concentration of at least about 80%. The resulting somatic polysaccharide-containing precipitate is isolated by centrifugation and redissolved in a conventional parenteral vehicle or formulated with a sustained release carrier such as those mentioned above. The concentration of somatic polysaccharide in the formulation will usually be in the range of 1 to 5 mg/ml.

Preferred vaccine formulations contain the purified forms of both surface polysaccharide and somatic polysaccharide, typically in a weight ratio (surface polysaccharide:somatic polysaccharide) of 3:1 to 1:3.

The acellular vaccines of the invention may be administered in a conventional manner to animals that are susceptible to infection by the pathogenic bacteria that was used to prepare the vaccine. Normally, subcutaneous, intradermal, or intramuscular injection is employed. The initial inoculation will typically be about 0.5 to 5 mcg active ingredient per kg body weight. Periodic boosters may be required to provide adequate protection against infection over prolonged time periods.

The following examples further illustrate the invention. These examples are not intended to limit the scope of the invention in any manner.

EXAMPLE 1

Haemophilus pleuropneumonia (HPP, strain ATCC 27089, serotype 2) were cultured overnight (37° C., pH 7.2) on brain-heart infusion agar (BHI). Ten ml of BHI broth were added to each culture plate. The bacteria were suspended therein by scraping and adjusted to an O.D. of 1.5 at 520 nm. Five ml of this suspension were added to 500 ml of BHI broth supplemented with 1% glycerol and incubated for 24 hours at 37° C., with shaking at 100 rpm. After this 24-hr period, 70 g of 5 mm cm diameter glass beads were added to the culture and the culture was shaken with the beads at 100 rpm at room temperature for 48 hr. The culture was then centrifuged at 4° C., 7000× g for 30 min and the supernatant was recovered. The bacterial pellet was resuspended in 200 ml of deionized water, and blended at high speed for 10 min at 4° C. The blend was centrifuged at 7000× g for 30 min and the supernatant was recovered and combined with the previously recovered supernatant.

Cetavlon (10% solution) was added to the combined supernatants to a final concentration of 1%. The mixture was stirred at ambient temperature for 30 min. The resulting precipitate was recovered from the mixture by centrifugation at 7000× g for 30 min. The somatic polysaccharide-containing supernatant was saved. The precipitate was solubilized in 200 ml of distilled water and an equal volume of 0.9 M NaCl was added followed by stirring for 1 hr at room temperature. Ethanol was then added to a final concentration of 25% and the mixture allowed to stand at room temperature for 2 hr. The surface polysaccharide precipitate was removed by centrifugation at 7000 x g, 4° C., for 30 min.

Additional ethanol was then added to the resulting supernatant to a final concentration of 80% and the resulting mixture was stirred for 1 hr at ambient temperature. The mixture was then centrifuged at 12,000×g at 4° C. for 45 min. The pellet was solubilized in 30 ml of 0.15 M phosphate-buffered saline (PBS) and the resulting solution was filter sterilized using a 0.22 micron filter.

Somatic polysaccharide was recovered from the somatic polysaccharide-containing supernatant by bringing the ethanol concentration to 80% and removing the resulting somatic polysaccharide precipitate by centrifugation at 12,000×g, 4° C. for 45 min. The final material was solubilized in 30 ml of 0.15 M PBS and filter sterilized. Alternatively, somatic polysaccharide is recovered by adding 1% Cetavlon to the supernatant and removing the resulting precipitate before bringing the ethanol concentration to 80%.

A final vaccine composition was prepared by combining 3 ml of the surface polysaccharide solution with 0.5 ml of the somatic polysaccharide solution.

This vaccine composition was mixed in a 1:1 volume ratio with a commercial oil adjuvant DM and tested in mice as follows. Mice were vaccinated intraperitoneally with the mixture at the following levels of surface polysaccharides: 50 mcg, 10 mcg, 2.5 mcg. The mice were boosted at one week at the same dose level and challenged with the bacteria one week after the boost. The vaccine provided protection, exhibiting a relative (to control) potency of 1.48 and a 50% protective dilution of 1:108.

EXAMPLE 2

A vaccine against HPP serotype 1 was prepared from HPP strain ATCC 27088 by the procedure of Example 1.

EXAMPLE 3

Vaccines against *Pasteurella haemolytica* and *Pasteurella multocida* are prepared according to the procedure of Example 1. The bacteria are cultured on BHI or yeast-cystine-proteose-peptone medium.

EXAMPLE 4

The vaccines of Examples 1 and 2 were tested on young swine. The animals were injected IM with 0.275 mg of vaccine in the case of HPP serotype 1 and 1 mg in the case of HPP serotype 2. The animals were boosted at the same dosage level two weeks after initial injection. Ten days after the booster the animals were challenged with the bacteria. Mortality and lung lesion scores were determined 7-10 days after challenge. Both vaccines provided protection as evidenced by lower mortality levels and lower average lung lesion scores than were observed in nonvaccinated control animals.

While the invention has been described with respect to gram-negative nonenteric bacilli, it may also be used to prepare surface polysaccharide compositions from pathogenic gram-positive bacilli.

Modifications of the above-described modes for carrying out the invention that are obvious to those of skill in the fields of biochemistry, vaccines or veterinary medicine are intended to be within the scope of the following claims.

We claim:

1. Process for preparing an acellular veterinary vaccine against a pathogenic bacilli from an aqueous suspension of the bacilli comprising:
   (a) mechanically shearing surface polysaccharide from the outer membrane of the bacteria without damaging the membrane;
   (b) separating the bacteria from the suspension to provide a surface polysaccharide-containing supernatant;
   (c) adding an organic cationic precipitating agent which does not degrade the surface polysaccharide to the supernatant to form a precipitate comprising an ionic complex of the agent and the surface polysaccharide;
   (d) separating the precipitate of (c) from the supernatant;
   (e) solubilizing the separated precipitate of (d) in an aqueous medium under conditions which cause the ionic complex to dissociate;
   (f) adding a sufficient amount of lower alkanol to the solution of (e) to cause nucleic acids to precipitate therefrom without substantial coprecipitation of the surface polysaccharide;
   (g) separating the precipitate of (f) from the solution;
   (h) thereafter increasing the concentration of lower alkanol in the solution to a level which causes the surface polysaccharide to precipitate therefrom; and
   (i) recovering the surface polysaccharide precipitate of (h).

2. The process of claim 1 wherein the bacilli is a gram-negative nonenteric bacilli.

3. The process of claim 2 wherein the mechanical shearing is achieved by agitating the suspension in contact with particulate abrasive means.

4. The process of claim 3 wherein the particulate abrasive means is glass beads.

5. The process of claim 3 wherein the separations of steps (b), (d) and (g) are achieved by centrifugation.

6. The process of claim 2 wherein the organic cationic precipitating agent is a quaternary ammonium salt.

7. The process of claim 6 wherein the quaternary ammonium salt is hexadecyltrimethyl-ammonium bromide.

8. The process of claim 2 wherein the lower alkanol is ethanol.

9. The process of claim 2 wherein the pathogenic bacilli are of the Hemophilus or Pasteurella genera.

10. Process for preparing an acellular veterinary vaccine against a gram-negative nonenteric pathogenic bacilli from an aqueous suspension of the bacilli comprising:
   (a) mechanically shearing surface polysaccharide and somatic polysaccharide from the cell membrane of the bacteria without damaging the cell membrane;
   (b) separating the bacteria from the suspension to provide a surface polysaccharide- and somatic polysaccharide-containing supernatant;
   (c) adding an organic cationic precipitating agent which does not degrade the surface polysaccharide and somatic polysaccharide to the supernatant to form a precipitate comprising an ionic complex of the agent and the surface polysaccharide;
   (d) separating the precipitate of (c) from the supernatant;
   (e) thereafter adding a lower alkanol to the supernatant to a concentration which causes the somatic polysaccharide to precipitate therefrom; and (f) recovering the somatic polysaccharide precipitate of (e).

11. The process of claim 10 wherein the mechanical shearing is achieved by agitating the suspension in contact with particulate abrasive means.

12. The process of claim 10 wherein the separations of steps (b) and (d) and the recovery of step (f) are achieved by centrifugation.

13. The process of claim 10 wherein the organic cationic precipitating agent is a quaternary ammonium salt.

14. The process of claim 13 wherein the quaternary ammonium salt is hexadecyltrimethyl-ammonium bromide.

15. The process of claim 10 wherein the lower alkanol is ethanol.

16. The process of claim 10 wherein the bacilli are of the Hemophilus or Pasteurella genera.

17. A veterinary acellular vaccine against a gram-negative nonenteric pathogenic bacillus comprising a mixture of:
 (i) an injectable vehicle;
 (ii) the surface polysaccharide precipitate of step (i) of claim 2; and
 (iii) a somatic polysaccharide composition prepared from an aqueous suspension of the bacilli by
  (a) mechanically shearing surface polysaccharide and somatic polysaccharide from the cell membrane of the bacteria without damaging the cell membrane;
  (b) separating the bacteria from the suspension to provide a surface polysaccharide- and somatic polysaccharide-containing supernatant;
  (c) adding an organic cationic precipitating agent which does not degrade the surface polysaccharide and somatic polysaccharide to the supernatant to form a precipitate comprising a ionic complex of the agent and the surface polysaccharide;
  (d) separating the precipitate of (c) from the supernatant;
  (e) thereafter adding a lower alkanol to the precipitate to a concentration which causes the somatic polysaccharide to precipitate therefrom; and
  (f) recovering the somatic polysaccharide precipitate of (e).

18. The vaccine of claim 17 wherein the bacilli are of the Hemophilus or Pasteurella genera.

19. The vaccine of claim 17 wherein the weight ratio of (ii) to (iii) in the mixture is in the range of 1:3 to 3:1.

* * * * *